United States Patent [19]

Knops et al.

[11] Patent Number: 4,495,184

[45] Date of Patent: Jan. 22, 1985

[54] MORPHOLINO PROPANOL DERIVATIVES, FUNGICIDAL COMPOSITIONS AND USE

[75] Inventors: Hans-Joachim Knops; Wolfgang Krämer, both of Wuppertal; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 496,673

[22] Filed: May 23, 1983

[30] Foreign Application Priority Data

May 22, 1980 [DE] Fed. Rep. of Germany ....... 3019496

[51] Int. Cl.³ .................. A01N 43/84; C07D 295/08
[52] U.S. Cl. .................................. 514/238; 544/170; 544/171
[58] Field of Search ................ 544/170, 171; 421/248, 421/157

[56] References Cited

U.S. PATENT DOCUMENTS 3,151,124  9/1964  Huebner .......................... 544/171

FOREIGN PATENT DOCUMENTS 50-26549  9/1975  Japan .

OTHER PUBLICATIONS

Denton et al. (I), J. Amer. Chem. Soc., vol. 71 (1949) pp. 2054–2056.

Denton et al. (II) J. Amer. Chem. Soc., vol. 72 (1950) pp. 3795–3796.

Primary Examiner—Robert W. Ramsuer
Attorney, Agent, or Firm—Sprung, Horn, Kramer & Woods

[57] ABSTRACT

A 1-phenyl-3-amino-propane derivative of the formula

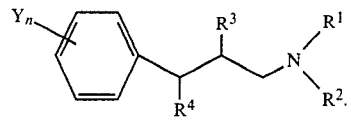

in which $R^1$ and $R^2$ independently represent alkyl radicals or $R^1$ and $R^2$ together with the nitrogen atom to which they are bonded complete an optionally substituted heterocyclic radical of the formula

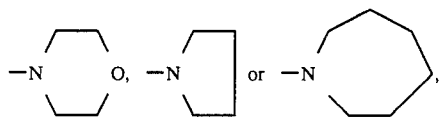

and or additionally, if $R^4$ represents the radical $-O-CO-R^5$, $-O-CO-NHR^6$ or $-O-SiR_3^7$, complete an optionally substituted heterocyclic radical of the formula

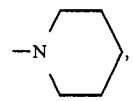

$R^3$ represents a hydrogen atom or an alkyl radical,
$R^4$ represents a hydroxyl group, halogen or the radical $-O-CO-R^5$, $-O-CO-NHR^6$ or $-O-SiR_3^7$,
$R^5$ represents an alkyl, alkenyl or halogenoalkyl radical or an optionally substituted aryl or aralkyl radical,
$R^6$ represents an alkyl or alkenyl radical or an optionally substituted aryl radical,
$R^7$ represents an alkyl radical each Y independently represents an alkyl radical, a halogen atom or a halogenoalkyl, alkoxy, alkylthio, halogenoalkoxy, halogenoalkylthio, cycloalkyl or cyano radical and
n is 0, 1, 2 or 3, or a physiologically acceptable acid addition salt thereof which possesses fungicidal activity.

6 Claims, No Drawings

MORPHOLINO PROPANOL DERIVATIVES, FUNGICIDAL COMPOSITIONS AND USE

This is a continuation of application Ser. No. 259,308, filed Apr. 30, 1981.

The present invention relates to certain new aminopropanol derivatives, to several processes for their production and to their use as fungicides.

It has already been disclosed that triazolylethanol derivatives, such as 1-(4-chlorophenyl)-2-(1,2,4-triazol-1-yl)-1-ethanol, in general have good fungicidal properties (see our U.S. Ser. No. 586,121, filed June 11, 1975), now abandoned; U.S. Ser. No. 792,756, filed May 2, 1977 is a continuation of U.S. Ser. No. 586,121. However, their action is not always completely satisfactory in some fields of use, especially when low amounts and concentrations are applied.

The present invention now provides as new compounds, the aminopropanol derivatives of the general formula

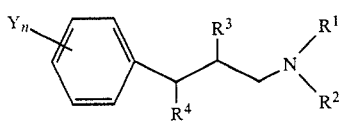

in which
 $R^1$ and $R^2$ independently represent alkyl radicals; or
 $R^1$ and $R^2$, together with the nitrogen atom to which they are bonded complete an optionally substituted heterocylic radical of the formula

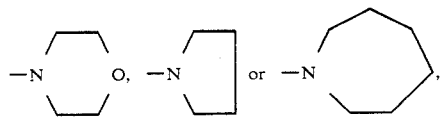

an or additionally, if $R^4$ represents the radical —O—O—C—$R^5$, —O—CO—NHR$^6$ or —O—SiR$_3^7$, complete an optionally substituted heterocyclic radical of the formula

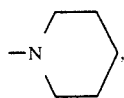

$R^3$ represents a hydrogen atom or an alkyl radical,
 $R^4$ represents a hydroxyl group, a halogen atom or a radical —O—CO—$R^5$, —O—OC—NHR$^6$ or —O—SiR$_3^7$,
 $R^5$ represents an alkyl, alkenyl or halogenoalkyl radical or an optionally substituted aryl or aralkyl radical,
 $R^6$ represents an alkyl or alkenyl radical or an optionally substituted aryl radical,
 $R^7$ represents an alkyl radical, each Y independently represents an alky radical a halogen atom or a halogenoalkyl, alkyoxy, alkylthio, halogenoalkoxy, halogenoalkylthio, cycloalkyl, or cyana radical and
 n is 0, 1, 2 or 3,
and physiologically acceptable acid addition salts thereof.

According to the present invention there is further provided a process for the production of an aminopropanol derivative of the present invention, characterized in that (a) an aminopropiophenone of the general formula

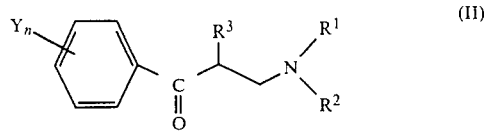

in which $R^1$, $R^2$, $R^3$, Y and n have the abovementioned meaning, is reduced with a complex hydride in the presence of a solvent to give an aminopropanol of the general formula

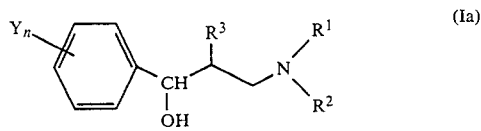

in which $R^1$, $R^2$, $R^3$, Y and n have the abovementioned meaning, (b), if a compound of formula (I) in which $R^4$ represents a halogen atom is required, the aminopropanol of formula (Ia) obtained as in reaction variant (a) is reacted with a halogenating agent, optionally in the presence of a solvent, and optionally in the presence of an acid-binding agent, or (c), if a compound formula (I) in which $R^4$ represents —O—CO—$R^5$, —O—CO—NHR$^6$ or —O—SiR$_3^7$ is required, the aminopropanol of formula (Ia) obtained as in reaction variant (a) is reacted with a halide of the general formula $$Hal—R^8 \qquad (III)$$

in which $R^8$ represents a radical —CO—$R^5$, —CO—NHR$^6$ or —SiR$_3^7$,
wherein
 $R^5$, $R^6$ and $R^7$ have the abovementioned meaning, and
 Hal represents a halogen atom in the presence of a solvent and optionally in the presence of a strong base, or optionally in the presence of an acid-binding agent, or (d), if a compound of formula (I) in which $R^4$ represents —O—CO—$R^5$ is required the aminopropanol of formula (Ia) obtained as in reaction variant (a) is reacted with an acid anhydride of the general formula $$R^5—CO—O—CO—R^5 \qquad (IV)$$

in which $R^5$ has the abovementioned meaning, in the presence of a solvent and optionally in the presence of a catalyst, or (e), if a compound of formula (I) in which $R^4$ represents —CO—NHR$^6$ is required, the aminopropanol of formula (Ia) obtained as in reaction variant (a) is reacted with an isocyanate of the general formula $$O=C=N—R^6 \qquad (V)$$

in which $R^6$ has the abovementioned meaning, in the presence of a solvent and optionally in the presence of a catalyst, and the product of reaction variant (a), (b), (c), (d) or (e) is converted, if desired, into a physiologically acceptable acid addition salt thereof.

The new aminopropanol derivatives of the present invention have powerful fungicidal properties. Surprisingly, the compounds according to the invention exhibit a more powerful action than 1-(4-chlorophenyl)-2-(1,2,4-triazoll-yl)-1-ethalnol, which is known from the state of the art and is a compound of the same type of action. The substances according to the invention thus represent an enrichment of the art.

Preferred aminopropanol derivatives according to the present invention are those in which $R^1$ and $R^2$ are identical or different and represent a straight-chain or branched alkyl radical with 1 to 4 carbon atoms, or $R^1$ and $R^2$, together with the nitrogen atom to which they are bonded, complete an optionally substituted heterocyclic radical of the formula

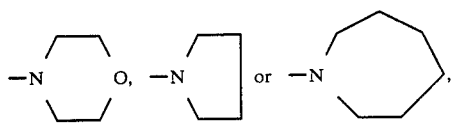

or in addition, if $R_7^4$ represents the radical —O—CO—$R^5$, —O—CO—NHR$^6$ or —O—SiR$_3^7$, complete an optionally substituted heterocyclic radical of the formula

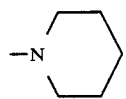

(preferred substituents being alkyl with 1 to 4 carbon atoms and a fused-on aromatic or alicyclic ring which has 5 to 7 carbon atoms and is optionally substituted by alkyl with 1 to 4 carbon atoms or halogen), $R^3$ represents a hydrogen atom or an alkyl radical with 1 to 4 carbon atoms, $R^4$ represents a hydroxyl group, a chlorine or bromine atom or a radical —O—CO—$R^5$, —O—CO—NHR$^6$ or —O—SiR$_3^7$, $R^5$ represents a straight-chain or branched alkyl radical with 1 to 4 carbon atoms, an alkenyl radical with 2 to 4 carbon atoms, a halogenoalkyl radical with 1 or 2 carbon atoms and 1 to 5 identical or different halogen atoms, (preferably fluorine and chlorine atoms), or an optionally substituted aryl radical with 6 to 10 carbon atoms or an aralkyl radical with 6 to 10 carbon atoms in the aryl part and 1 or 2 carbon atoms in the alkyl part (such as preferably, phenyl or benzyl, preferred substituents being halogen, alkyl with 1 to 4 carbon atoms, halogenoalkyl with 1 or 2 carbon atoms and 1 to 5 identical or different halogen atoms (preferably fluorine or chlorine atoms), and alkoxy and alkylthio with in each case 1 or 2 carbon atoms), $R^6$ represents a straight-chain or branched alkyl radical with 1 to 8 carbon atoms, an alkenyl radical with 2 to 4 carbon atoms or an optionally substituted aryl radical with 6 to 10 carbon atoms (such as, in preferably, phenyl, preferred possible substituents being the substituents on phenyl which have already been mentioned above), $R^7$ represents a straight-chain or branched alkyl radical with 1 to 4 carbon atoms, each Y independently represents a straight-chain or branched alkyl radical with 1 to 4 carbon atoms, a halogen atom, a halogenating radical with 1 or 2 carbon atoms and 1 to 5 halogen atoms (halogens which may be mentioned as preferences being fluorine and chlorine), and alkoxy or alkylthio radical with in each case 1 or 2 carbon atoms, a halogenoalkoxy or halogenoalkylthio radical with 1 or 2 carbon atoms and 2 to 5 halogen atoms (halogens which may be mentioned as preferences being fluorine and chlorine), a cycloalkyl radical with 3 to 7 carbon atoms or a cyano radical, and n is 0, 1 or 2.

Particularly preferred aminopropanol derivatives of the present invention are those in which $R^1$ and $R^2$ independently represent an alkyl with 1 to 4 carbon atoms or, together with the nitrogen atom to which they are bonded, complete an optionally substituted heterocyclic radical of the formula

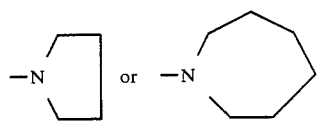

or, in addition, if $R^4$ represents the radical —O—CO—$R^5$, —O—CO—NHR$^6$ or —O—SiRhd 3$^7$, complete an optionally substituted heterocyclic radical of the formula

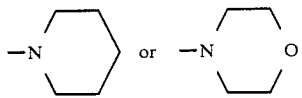

(possible substituents being methyl, ethyl or a fused-on benzene or cyclohexyl ring), $R^3$ represents a hydrogen atom or a methyl radical, $R^4$ represents a hydroxyl group, a chlorine or bromine atom or a radical —O—CO—$R^5$, —O—CO—NHR$^6$ or —OSiR$_3^7$, $R^5$ represents a methyl, ethyl, isopropyl, isobutyl, chloromethyl or dichloromethyl radical, or an optionally monosubstituted or polysubstituted phenyl or benzyl radical with chlorine, bromine, methyl or trifluoromethyl as substituents, $R^6$ represents a straight-chain or branched alkyl radical with 1 to 4 carbon atoms or optionally monosubstituents or polysubstituted phenyl radical with chlorine, bromine, methyl or trifluoromethyl as substituents, $R^7$ represents a methyl or ethyl radical, each Y independently represents a methyl, isopropyl, tert.-butyl, fluorine, chlorine, trifluoromethyl or cyclohexyl radical and n is 0, 1 or 2.

The following compounds of the general formula (I) may be mentioned specifically, in addition to the compounds mentioned in the preparative examples:

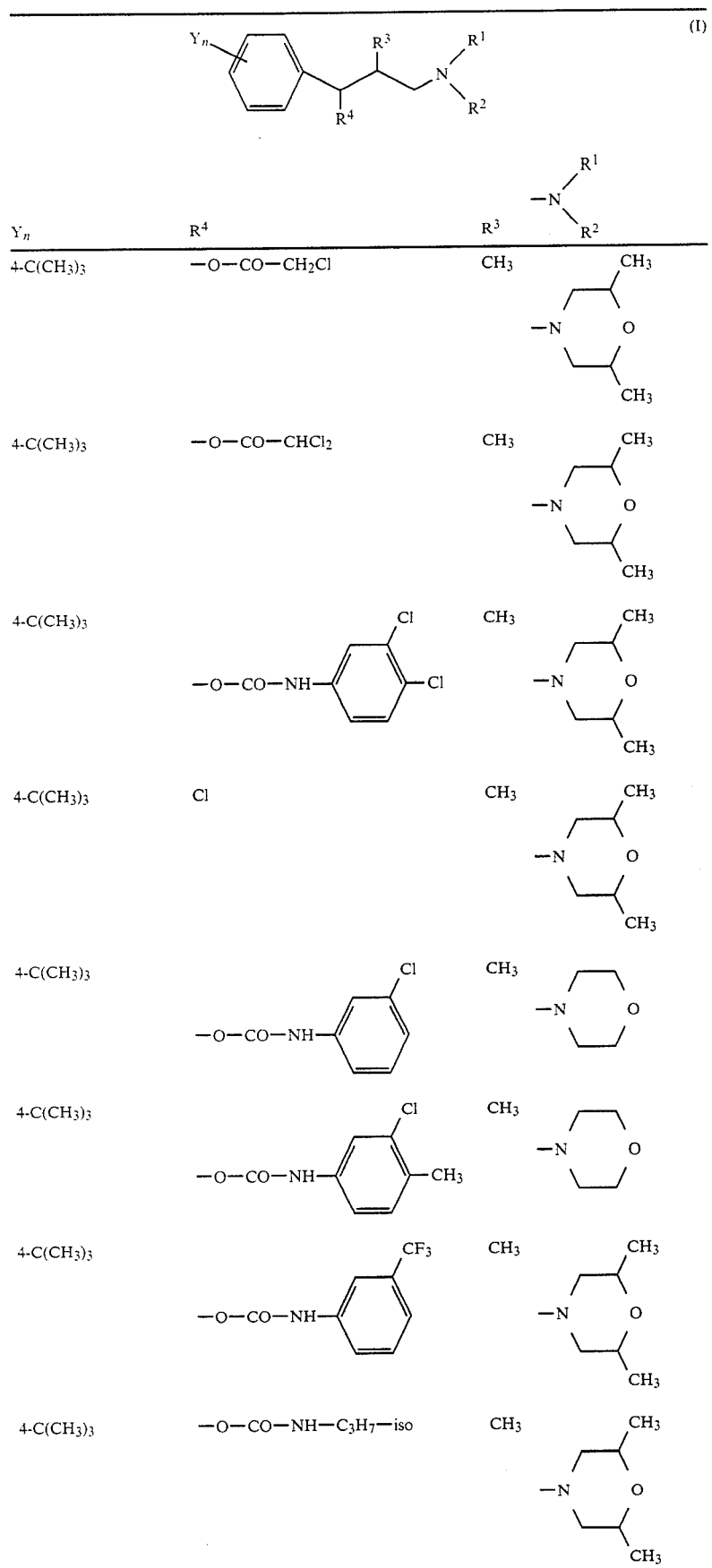

-continued $$Y_n \underset{R^4}{\overset{R^3}{-}} \underset{}{\overset{}{-}} N \underset{R^2}{\overset{R^1}{}} \quad (I)$$

| $Y_n$ | $R^4$ | $R^3$ | $-N\begin{matrix}R^1\\R^2\end{matrix}$ |
|---|---|---|---|
| 4-C(CH$_3$)$_3$ | —O—CO—NH—CH$_3$ | CH$_3$ | 2,6-dimethylmorpholino |
| 4-C(CH$_3$)$_3$ | —O—CO—NH—C$_4$H$_9$—iso | CH$_3$ | 2,6-dimethylmorpholino |
| 4-C(CH$_3$)$_3$ | —O—CO—NH—C$_4$H$_9$—n | CH$_3$ | 2,6-dimethylmorpholino |
| 4-C(CH$_3$)$_3$ | —O—CO—NH—C$_4$H$_9$—n | CH$_3$ | piperidino |
| 4-C(CH$_3$)$_3$ | —O—CO—NH—C$_4$H$_9$—iso | CH$_3$ | piperidino |
| 4-C(CH$_3$)$_3$ | —O—CO—NH—CH$_3$ | CH$_3$ | piperidino |
| 4-C(CH$_3$)$_3$ | —O—CO—NH—C$_3$H$_7$—iso | CH$_3$ | piperidino |
| 4-C(CH$_3$)$_3$ | —O—CO—NH—(3-CF$_3$-C$_6$H$_4$) | CH$_3$ | piperidino |
| 4-C(CH$_3$)$_3$ | —O—CO—NH—(3-Cl-4-CH$_3$-C$_6$H$_3$) | CH$_3$ | piperidino |

-continued
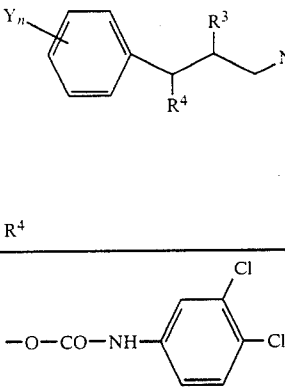 (I)
| $Y_n$ | $R^4$ | $R^3$ | $-N\begin{smallmatrix}R^1\\R^2\end{smallmatrix}$ |
|---|---|---|---|
| 4-C(CH$_3$)$_3$ | 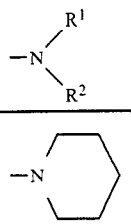 | CH$_3$ | 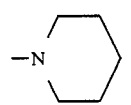 |
| 4-C(CH$_3$)$_3$ | —O—CO—CHCl$_2$ | CH$_3$ | 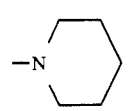 |
| 4-C(CH$_3$)$_3$ | —O—CO—CH$_2$Cl | CH$_3$ | 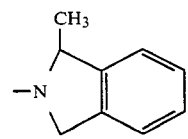 |
| 4-C(CH$_3$)$_3$ | —OH | CH$_3$ | 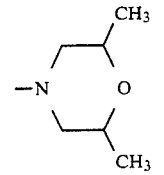 |
| 4-C(CH$_3$)$_3$ | —OH | CH$_3$ | —N(C$_2$H$_5$)$_2$ |
| 4-C(CH$_3$)$_3$ | —OH | CH$_3$ | —N(C$_3$H$_7$—iso)$_2$ |
| 4-C(CH$_3$)$_3$ | —OH | CH$_3$ | —N(C$_3$H$_7$—n)$_2$ |
| 4-C(CH$_3$)$_3$ | —OH | CH$_3$ | —N(C$_4$H$_9$—n)$_2$ |
| 4-C(CH$_3$)$_3$ | —OH | CH$_3$ | —N(C$_4$H$_9$—iso)$_2$ |
| 4-Cl | —OH | CH$_3$ | 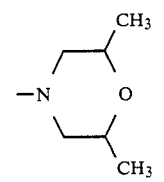 |
| 2,4-Cl$_2$ | —OH | CH$_3$ | 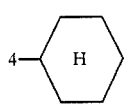 |
| 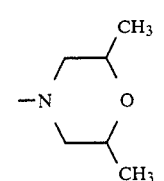 | —OH | CH$_3$ | 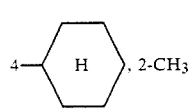 |
| 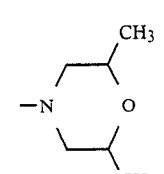 | —OH | CH$_3$ | 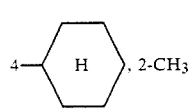 |

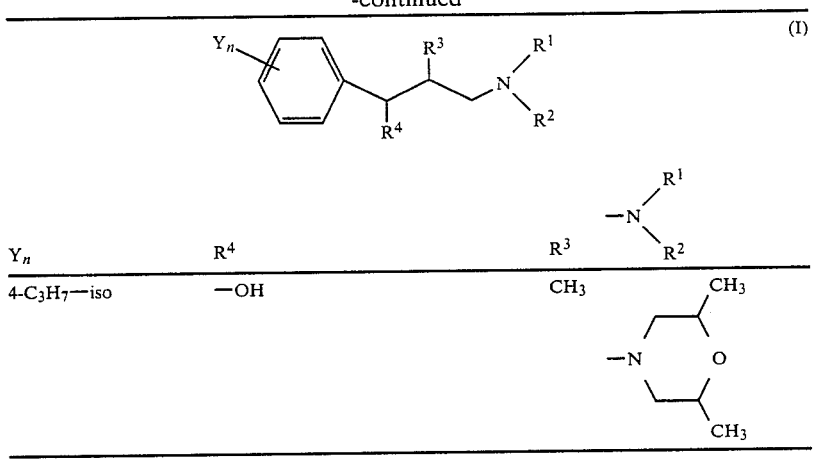

If p-tert.-butyl-2-methyl-3-morpholin-4-yl-propiophenone and sodium borohydride are used as starting substances, the course of the reaction for the preparation of compounds of the invention is illustrated by the following equation (process variant (a)):

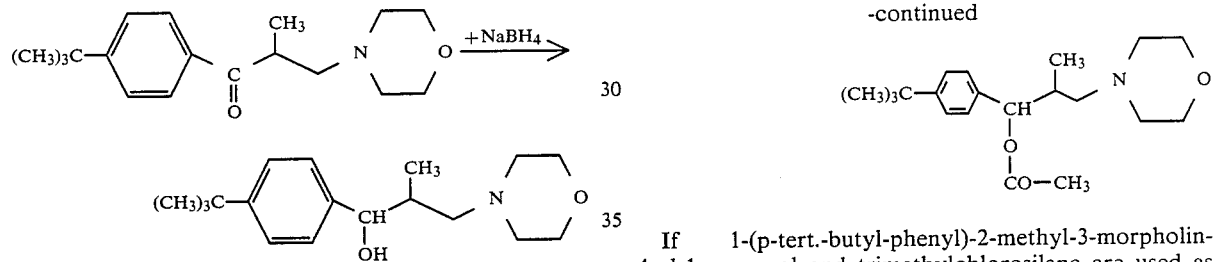

If 1-(p-tert.-butyl-phenyl)-2-methyl-3-morpholin-4-yl-1-propanol and thionyl chloride are used as starting substances, the course of the reaction for the preparation of compounds of the invention is illustrated by the following equation (process variant (b)):

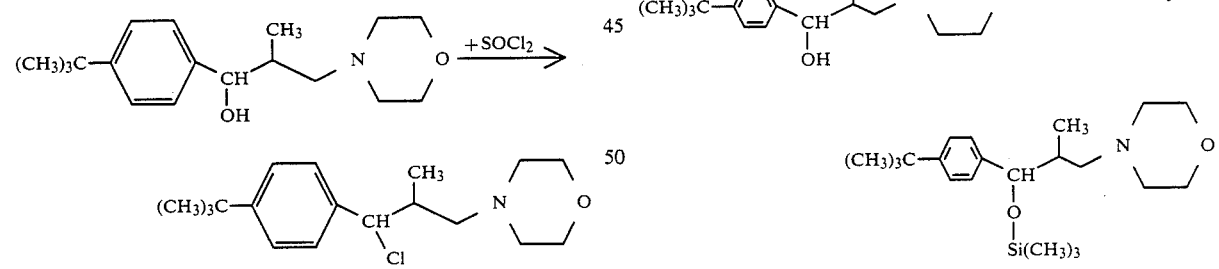

If 1-(p-tert.-butyl-phenyl)-2-methyl-3-morpholin-4-yl-1-propanol and acetyl chloride are used as starting substances, the course of the reaction for the preparation of compounds of the invention is illustrated by the following equation (process variant (c)):

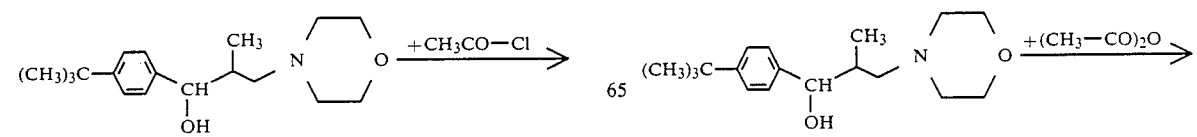

If 1-(p-tert.-butyl-phenyl)-2-methyl-3-morpholin-4-yl-1-propanol and trimethylchlorosilane are used as starting substances, the course of the reaction for the preparation of compounds of the invention is illustrated by the following equation (process variant (c)):

If 1-(p-tert.-butyl-phenyl)-2-methyl-3-morpholin-4-yl-1-propanol and acetic anhydride are used as starting substances, the course of the reaction for the preparation of compounds of the invention is illustrated by the following equation (process variant (d)):

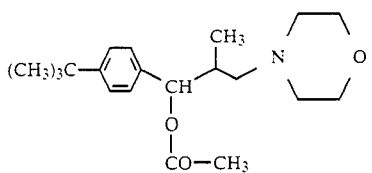

If 1-(p-tert.-butyl-phenyl)-2-methyl-3-morpholin-4-yl-1-propanol and phenyl isocyanate are used as starting substances, the course of the reaction for the preparation of compounds of the invention is illustrated by the following equation (process variant (e)):

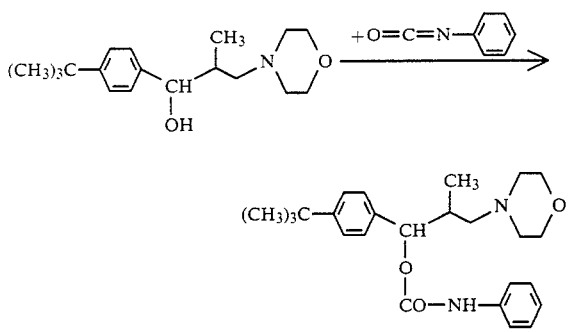

Preferred aminopropiophenones of formula (II) to be used as starting substances for process variant (a) according to the invention are those in which $R^1$, $R^2$, $R^3$, Y and n have those meanings which have already been mentioned in connection with the description of the preferred and particularly preferred compounds according to the invention. E Aminopropiophenones of the formula (II) are known (see published European Patent application No. 0,005,541); they are obtained by reacting a known acetophenone of the general formula

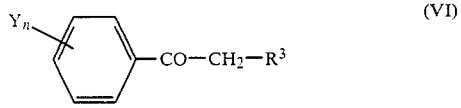

in which $R^3$, Y and n have the abovementioned meanings, with paraformaldehyde and with an amine of the general formula

in which $R^1$ and $R^2$ have the abovementioned meanings, in the presence of a protic solvent, such as ethanol, at temperatures between 50 and 120° C., the amine of the formula (VII) preferably being employed as the hydrochloride.

The complex hydrides also required as starting substances for process variant (a) according to the invention are generally known compounds of organic chemistry. Examples which may be mentioned are, as preferences, sodium borohydride and lithium alanate.

The aminopropanols of the formula (Ia) to be used as starting substances for process variants (b), (c), (d) and (e) according to the invention are compounds according to the invention.

The halogenating agents also required for process variant (b) according to the invention are generally known compounds or organic chemisry. Examples which may be mentioned are, preferably, inorganic acid halides, such as phosphorus trichloride, tribromide and pentachloride, phosphorus oxychloride and thionyl chloride.

Preferred halides of formula (III) also to be used as starting substances for process variant (c) according to the invention are those in which $R^8$ represents the radical -CO-$R^5$, -CO-NH$R^6$ or Si$R_3^7$ and $R^5$, $R^6$ and $R^7$ representing those radicals which have already been mentioned for these substituents in connection with the description of the preferred and particularly preferred compounds according to the invention, and Hal represents a fluorine, chlorine or bromine atom.

The halides of the formula (III) are generally known compounds of organic chemistry.

Preferred acid anhydrides of formula (IV) also to be used as starting substances for process variant (d) according to the invention are those in which $R^5$ represents those radicals which have already been mentioned for this substituent in connection with the description of the preferred and particularly preferred compounds according to the invention.

The acid anhydrides of the formula (IV) are generally known compounds if organic chemistry.

Preferred isocyanates of formula (V) also to be used as starting substances for process variant (e) according to the invention are those in which $R^6$ represents those radicals which have alredy been mentioned for this substituent in connection with the description of the preferred and particularly preferred compounds according to the invention.

The isocyanates of the formula (V) are generally known compounds of organic chemistry.

Preferred solvents for process variant (a) according to the invention are polar organic solvents. These include, preferably, alcohols (such as methanol, ethanol, isopropanol or butanol) and ethers (such as diethyl ether or tetrahydrofuran).

The reaction temperatures can be caried within a substantial range in carrying out process variant (a) according to the invention. In general, the reaction is carried out at a temperature between 0° and 60° C., preferably at a temperature between 0° and 40° C.

Equimolar amounts are preferably used in carrying out process variant (a) according to the invention. The end products are isolated in the generally customary manner, if appropriate also as the acid addition salt.

Preferred solvents for variant process (b) according to the invention are inert organic solvents. These include, preferably, amides (such as dimethylformamide), sulphoxides (such as dimethylsulphoxide), and petroleum ether. In particular, it is also possible to employ an excess of the particular inorganic acid halide used as the diluent.

Preferred possible acid-binding agents for process variant (b) according to the invention are organic bases, such as pyridine and triethylamine.

The reaction temperatures can be varied within a substantial range in carrying out process variant (b) according to the invention. In general, the reaction is carried out a temperature between −20° and 100° C., preferably at a temperature between −10° and 80° C.

Equimolar amounts are preferably used in carrying out process variant (b) accoding to the invention. For simplicity, the halogenating agent employed can also be used as the solvent, whereupon an appropriate excess will be required. The compounds of the formula (I) are isolated by removing excess halogenating agent, for example by distillation, adding aqueou sodium bicarbonate solution to the reaction mixture and extracting the reaction product by shaking the mixture with an organic solvent.

Preferred possible solvents for process variant (c) according to the invention are inert organic solvents. These include, preferably, ethers (such as diethyl ether and dioxane), aromatic hydrocarbons (such as toluene and benzene), in individual cases also chlorinated hydrocarbons (such as chloroform, methylene chloride or carbon tetrachloride), and ketones (such as acetone or methyl ethyl keton), nitriles (such as acetonitrile) and petroleum ether. For simplicity, an acid halide employed can optionally also be used as the solvent, whereupon an appropriate excess will be required.

The reaction temperatures can be varied within a substantial range in carrying out process (c) according to the invention. In general, the rection is carried out at a temperature between 20° and 150° C., preferably at a temperature between 20° and 100° C., or at the boiling point of the particular solvent.

If appropriate, process variant (c) according to the invention can be carried out in the presence of a strong base. Strong bases include, as preferences, alkali metal hydrides, alkali metal amides and alkali metal alcoholates, such as sodium hydride, sodium amide and potassium tert.-butylate.

If appropriate, process variant (c) according to the invention can be carried out in the presence of acid-binding agents (hydrogen halide acceptors). These include organic bases, preferably tertiary amines (such as triethylamine) and also inorganic bases (such as alkali metal hydroxides and alkali metal carbonates).

In carrying out process variant (C) according to the invention, 1 to 3 moles of halide of the formula (III) are preferbly employed per mole of the compounds of the formula (Ia). In order to isolate the end products, for example, the reaction mixture is freed from the solvent, and water and an organic solvent are added to the residue. The organic phase is separated off and worked up in the customary manner.

In a preferred embodiment, it is expedient to follow a procedure in which a compound of the formula (Ia) (obtained according to reaction variant (a)) is used as the starting material, this compound is converted into the alkanolate by means of an alkali metal hydride or alkali metal amide, in a suitable inert organic solvent, and the alkanolate is reacted immediately without being isolated, with a halide of the formula (III), the compounds of the formula (I) according to the invention being obtained in one operation, with elimination of an alkali metal halide.

Preferred possible solvents for process variant (d) according to the invention are inert oranic solvents. These include, preferably, the solvents listed in the case of process variant (c), and an exces of the particular acid anhydride of the formula (IV) which is used.

Catalysts which can be used in process variant (D) are, preferably, any of the customary acid and basic catalysts, such as sulphuric acid, hydrogen chloride, hydrogen bromide, boron trifluoride, zinc chloride, sodium acetate, sodium benzoate, sodium carbonate, calcium oxide, magnesium oxide, pyridine and triethylamine.

The reaction temperatures can be varied within a substantial range in carrying out process variant (d) according to the invention. In general, the reaction is carried out at a temperature between 20° and 150° C., preferably at a temperature between 50° C.

Equivalent amounts of starting substances are preferably used in carrying out process variant (d). For simplicity, the acid anhydride of the formula (IV) employed can also be used as the solvent, whereupon an appropriate excess will be required. The compounds of the formula (I) are isolated in the customary manner.

Preferred possible solvents for process variant (e) according to the invention are inert organic solvents. These include, preferably, the solvents listed in the case of process variant (c).

Catalysts which can be used in process variant (e) are, preferably; tertiary bases (such as triethylamine and pyridine) or organo-tin compounds (such as dibutyl-tin dilaurate and tributyl-tin laurate).

The reaction temperatures can be varied within a substantial range in carrying out process (e) according to the invention. In general, the reaction is carried out at a temperature between 0° and 100° C., preferably at the boiling point of the solvent used.

Equivalent amounts of starting substances are preferably used in carrying out process variant (d). For simplicity, the acid anhydride of the formula (IV) employed can also be used as the solvent, whereupon an appropriate excess will be required. The compounds of the formula (I) are isolated in the customary manner.

Preferred possible solvents for process variant (e) according to the invention are inert organic solvents. These include, preferably, the solvents listed in the case of process variant (c).

Catalysts which can be used in process variant (e) are, preferably; tertiary bases (such as triethylamine and pyridine) or organo-tin compounds (such as dibutyl-tin dilaurate and tributyl-tin laurate).

The reaction temperatures can be varied within a substantial range in carrying out process (e) according to the invention. In general, the reaction is carried out at a temperature between 0° and 100° C., preferably at the boiling point of the solvent used.

Equivalent amounts of starting substances are preferably used in carrying out process variant (e) according to the invention. In order to isolate the compounds of the formula (I), the solvent is distilled off and the residue is worked up by customary methods.

The substances of the formula (I), according to the invention, which can be prepared by process variant (a) to (e) can be converted into acid addition salts.

The following acids can preferably be used for the preparation of physiologically acceptable acid addition salts of the compounds of the formula (I): hydrogen halide acids (such as hydrobromic acid and, preferably, hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicyclic acid, sorbic acid and lactic acid) and sulphonic acids (such as p-toluenesulphonic acid and 1,5-naphthalene-disulphonic acid).

The acid addition salts of the compounds of the formula (I) can be obtained in a simple manner by customary salt formation methods, for example by dissolving a compound of the formula (I) in a suitable inert solvent and adding the acid, for example hydrogen chloride, and they can be isolated in a known manner, for example by filtration, and if appropriate purified by washing with an inert organic solvent.

The active compounds according to the invention exhibit a power microbicidal action and can be employed in practice for combating undesired microorganisms. The active compounds are suitable for use as plant protection agents.

Fungicidal agents in plant protection are employed for combating *Plasmodiophoromycetes, Oomycetes, Chytridiomycetes, Zygomycetes, Ascomycetes, Basidiomycetes* and *Deuteromycetes.*

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be employed with particularly good success for combating those fungi which cause powdery mildew diseases, thus, for combating *Erysiphe* species, such as against the powdery mildew of barley or of cereal causative organism (*Erysiphe graminis*); and for combating those fungi which cause scab and rust diseases, thus, for combating *Venturia* species, such as against the apple scab causative organism (*Fusicladium dendriticum*), and *Uromyces* species, such as against the bean rust causative organism (*Uromyces phaseoli*). The active compounds according to the invention also exhibit a good in vitro fungicidal action against *Fusarium nivale.*

When applied in certain amounts, the substances according to the invention also exhibit a growth-regulating action.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for exxample, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dye-stuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02%, are required at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

Process Variant (a)
(i) Preparation of the starting material

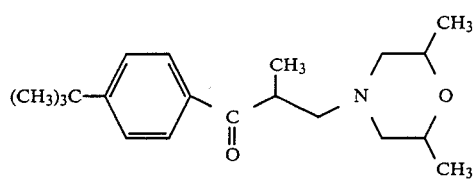

57.6 g (0.5 mole) of 2,6-dimethylmorpholine hydrochloride, 95.2 g (0.5 mole) of p-tert.-butyl-propiophenone and 25 g (0.83 mole) of paraformaldehyde were heated under reflux in 200 ml of ethanol for 1 hour. After adding 0.7 ml of concentrated hydrochloric acid, the reaction mixture was stirred under reflux for a further 15 hours. It was then concentrated, the residue was taken up in chloroform and the chloroform mixture was washed twice with water, dried over sodium sulphate and concentrated. The solid residue was suspended in hot ethyl acetate, filtered off and dried. 47.6 g (30% of theory) of p-tert.-butyl-2-methyl-3-(2,6-dimethylmorpholin-4yl)-propionphenone hydrochloride were obtained and were dissolved in aqueous sodium bicarbonate solution and the solution and 25 g (0.83 mole) of paraformaldehyde were heated under reflux in 200 ml of ethanol for 1 hour. After adding 0.7 ml of concentrated hydrochloric acid, the reaction mixture was stirred under reflux for a further 15 hours. It was then concentrated, the residue was taken up in chloroform and the chloroform mixture was washed twice with water, dried over sodium sulphate and concentrated. The solid residue was suspended in hot ethyl acetate, filtered off and dried. 47.6 g (30% of theory) of p-tert.-butyl-2-methyl-3-(2,6-dimethylmorpholin-4yl)-propionphenone hydrochloride were obtained and were dissolved in aqueous sodium bicarbonate solution and the solution was then extracted with ethyl acetate and the product phase concentrated. A quantative yield of the free base of boiling point 145°–48° C./0.12 mm Hg column was obtained.

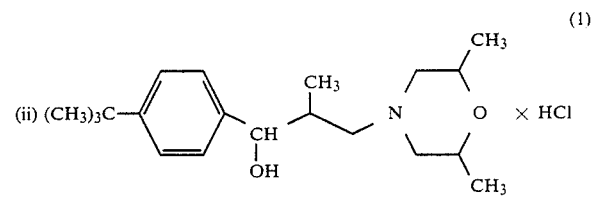

18.3 g (0.06 mole) of p-tert.-butyl-2-methyl-3-(2,6-dimethylmorpholin-4-yl)-propiophenone were initially introduced into 150 ml of methanol, and 2.5 g (0.06 mole) of sodium borohydride were added in portions, during which the temperature was not allowed to exceed 40° C. The mixture was subsequently stirred at room temperature for 3 hours and concentrated, the residue was taken up in 100 ml of water and dilute hydrochloric acid was added until the pH value is 1. The precipitate formed was filtered off and dried. 14.4 g (67.4% of theory) of 1-(p-tert.-butyl-phenyl)-2-methyl-3-(2,6-dimethylmorpholin-4-yl)-1-propanol hydrochloride of melting point 243° C. were obtained.

Example 2

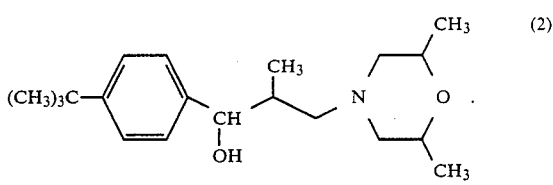

The hydrochloride obtained according to Example 1 was dissolved in aqueous sodium bicarbonate solution, the solution was then extracted with ethyl acetate and the product phase was concentrated. A quantitative yield of 1-(p-tert.-butyl-phenyl)-2-methyl-3-(2,6-dimethylmorpholin-4-yl)-1-propanol of melting point 49°–50° C. was obtained.

Example 3

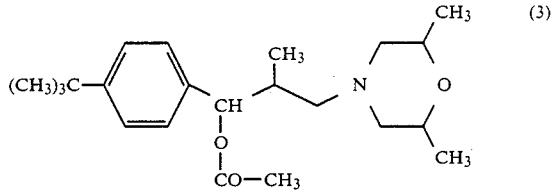

Process variant (d)
7.2 g (0.02 mole) of 1-(p-tert.-butyl-phenyl)-2-methyl-3-(2,6-dimethylmorpholin-4-yl)-1-propanol (obtained according to Example 2) were stirred in 50 ml of acetic anhydride to room temperature for 3 hours. The reaction mixture was then introduced into 100 ml of water and the mixture was adjusted to a pH value of 7 with dilute sodium hydroxide solution and extracted with chloroform. The organic phase was dried over sodium sulphate and concentrated. The oily residue was taken up in ethyl acetate, the ethyl acetate mixture was shaken with active charcoal and filtered and the filtrate was concentrated. The resulting oil was digested with petroleum ether, a brown precipitate was separated off and the mixture was concentrated. 5.3 g (73% of theory) of 1-acetoxy-1-(p-tert.-butyl-phenyl)-2-methyl-3-

(2,6-dimethylmorpholin-4-yl)-propane were obtained as a viscous oil.

EXAMPLE 4

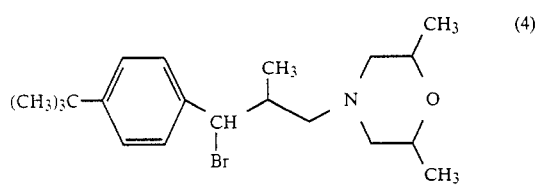

Process variant (b)

21.6 g (0.07 mole) of 1-(p-tert.-butyl-phenyl)-2-methyl-3-(2,6-dimethylmorpholin-4-yl)-1-propanol (obtained according to Example 2) were dissolved in 250 ml of petroleum ether with 1.9 ml of pyridine and a solution of 2.9 ml (0.03 mole) of phosphorus tribromide in 50 ml of petroleum ether was added dropwise at −5° to −10° C. The mixture was subsequently stirred at room temperature for 3 hours and the precipitate was filtered off, washed with petroleum ether and dissolved in chloroform. The chloroform phase was washed with sodium bicarbonated solution, dried over sodium sulphate and concentrated in vacuo. 23 g (88% of theory) of 1-bromo-1-(p-tert.-butyl-phenyl)-2-methyl-3-(2,6-dimethylmorpholin-4-yl)-propane were obtained as a viscous oil.

Example 5

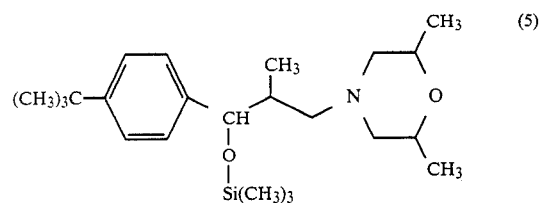

Process variant (c)

10 g (0.03 mole) of 1-(p-tert.-butyl-phenyl)-2-methyl-3-(2,6-dimethylmorpholin-4-yl)-1-propanol (obtanied according to Example 2) were dissolved in 160 ml of petroleum ether with 4.4 ml of triethylamine at room temperature and 3.4 g of trimethylchlorosilane in 40 ml of petroleum ether were added dropwise. The precipitate was filtered off and the filtrate was concentrated. 12 g (98% of theory) of 1-(p-tert.-butyl-phenyl)-1-trimethylsilyloxy-2-methyl-3-(2,6-dimethylmorpholin-4-yl)-propane were obtained as a viscous oil.

Example 6

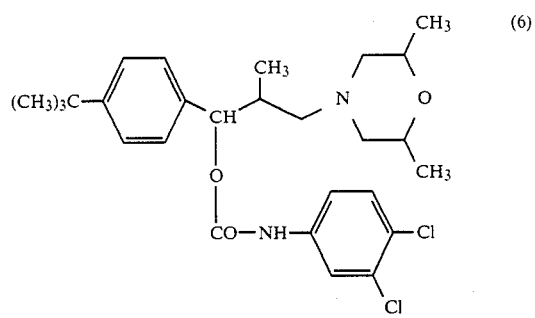

Process variant (e)

6.8 g (0.021 mole) of 1-(p-tert.-butyl-phenyl)-2-methyl-3-(2,6-dimethylmorpholin-4-yl)-1-propanol (obtained according to Example 2) and 0.6 mole of triethylamine were dissolved in 60 ml of acetonitrile, and a solution of 4.0 g of 3,4-dichlorophenyl isocyanate in 10 ml of acetonitrile was added dropwise at room temperature. The mixture was subsequently stirred under reflux for one hour, cooled and concentrated. The residue was taken up in ethyl acetate and the ethyl acetate was washed with water, dried over sodium sulphate and concentrated. 8.2 g (70% of theory) of 1-(p-tert.-butyl-phenyl)-1-(3,4-dichlorophenyl-carbamoyloxy)-2-methyl-3-(2,6-dimethylmorpholin-4-yl)-propane were obtained as a viscous oil.

The following compounds of the general formula

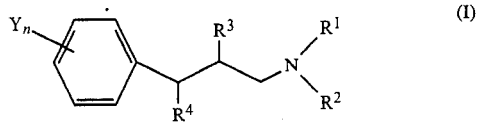

were obtained in a corresponding manner and according to the process variants given above:

| Compound No. | $Y_n$ | $R^4$ | $R^3$ | $-N\begin{smallmatrix}R^1\\R^2\end{smallmatrix}$ | Melting point (°C.) or boiling point (°C.) mm Hg Column |
|---|---|---|---|---|---|
| 7 | 4-C(CH₃)₃ | —OH | CH₃ | —N(morpholino) | 253(decomposition)(× HCl) |
| 8 | 4-C(CH₃)₃ | —OH | CH₃ | —N(azepane) | 228–29 (× HCl) |
| 9 | 4-C(CH₃)₃ | —OH | CH₃ | —N(pyrrolidine) | 211–15 (× HCl) |

-continued

| Compound No. | $Y_n$ | $R^4$ | $R^3$ | $-N\begin{smallmatrix}R^1\\R^2\end{smallmatrix}$ | Melting point (°C.) or boiling point (°C.) mm Hg Column |
|---|---|---|---|---|---|
| 10 | 4-C(CH$_3$)$_3$ | Cl | CH$_3$ | 2,6-dimethylmorpholino | oil |
| 11 | 4-C(CH$_3$)$_3$ | —O—CO—NH—(3,4-dichlorophenyl) | CH$_3$ | piperidino | oil |
| 12 | 4-C(CH$_3$)$_3$ | —O—Si(CH$_3$)$_3$ | CH$_3$ | piperidino | oil |
| 13 | 4-C(CH$_3$)$_3$ | OH | CH$_3$ | —N(C$_2$H$_5$)$_2$ | 185 (× HCl) |
| 14 | 4-C(CH$_3$)$_3$ | OH | CH$_3$ | —N(C$_3$H$_7$)$_2$ | 152 (× HCl) |
| 15 | 4-C(CH$_3$)$_3$ | Cl | CH$_3$ | —N(C$_3$H$_7$)$_2$ | 145 |
| 16 | 4-C(CH$_3$)$_3$ | —O—CO—NH—(3-chloro-4-methylphenyl) | CH$_3$ | 2,6-dimethylmorpholino | oil |
| 17 | 4-C(CH$_3$)$_3$ | —O—CO—NH—(3-chlorophenyl) | CH$_3$ | 2,6-dimethylmorpholino | oil |
| 18 | 4-C(CH$_3$)$_3$ | —O—CO—NH—(3-trifluoromethylphenyl) | CH$_3$ | 2,6-dimethylmorpholino | oil |
| 19 | 4-C(CH$_3$)$_3$ | —O—CO—NH—C$_3$H$_7$—i | CH$_3$ | 2,6-dimethylmorpholino | oil |
| 20 | 4-C(CH$_3$)$_3$ | —O—CO—NH—CH$_3$ | CH$_3$ | 2,6-dimethylmorpholino | oil |

-continued

| Compound No. | $Y_n$ | $R^4$ | $R^3$ | $-N\begin{smallmatrix}R^1\\R^2\end{smallmatrix}$ | Melting point (°C.) or boiling point (°C.) mm Hg Column |
|---|---|---|---|---|---|
| 21 | 4-C(CH₃)₃ | —O—CO—NH—CH₂—C₃H₇—i | CH₃ | morpholine (2,6-diCH₃) | Oil |
| 22 | 4-C(CH₃)₃ | —O—CO—NH—C₄H₉—n | CH₃ | morpholine (2,6-diCH₃) | Oil |
| 23 | 4-C(CH₃)₃ | —O—CO—CH₂Cl | CH₃ | morpholine (2,6-diCH₃) | 174–82 (× HCl) |
| 24 | 4-C(CH₃)₃ | —O—CO—CHCl₂ | CH₃ | morpholine (2,6-diCH₃) | 171–78 (× HCl) |
| 25 | 4-C(CH₃)₃ | —O—Si(CH₃)₃ | CH₃ | morpholine | Oil |
| 26 | 4-C(CH₃)₃ | OH | CH₃ | —N(C₃H₇—i)₂ | 206 (× HCl) |
| 27 | 4-C(CH₃)₃ | OH | CH₃ | —N(—CH₂—C₃H₇—i)₂ | Oil (× HCl) |
| 28 | 4-C(CH₃)₃ | OH | CH₃ | —N(C₄H₉—n)₂ | Oil (× HCl) |

The fungicidal activity of the compounds of this invention is illustrated by the following biotest example wherein the compounds according to the present invention are each identified by the number (given in brackets) from the preparative examples hereinabove.

The known comparison compound is identified as follows:

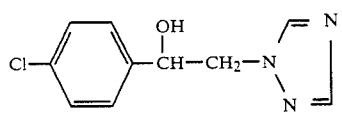

Example 6

Erysiphe test (barley)/protective/

Solvent: 100 parts by weight of dimethyl formamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of Erysiphe graminis f.sp. hordei.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a significantly superior activity compared with the prior art compound (A) shown, for example, by the compounds (2), (3), (4) and (7).

It will be appreciated that the instant specification and examples are set forth by way of illustration and not limitation, and that various modifications and changes may be made without departing from the spirit and scope of the present invention.

I claim:

1. A 1-phenyl-3-amino-propane derivative of the formula

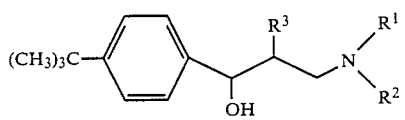

in which
- $R^1 R^2$ together with the nitrogen atom to which they are bonded form a morpholino ring, optionally substituted by one or more methyl groups, and
- $R^3$ is selected from the group consisting of a hydrogen atom and an alkyl radical, or a physiologically acceptable acid addition salt thereof.

2. A compound according to claim 1, wherein such compound is 1-(p-tert.-butyl-phenyl)-2-methyl-3-(2,6-dimethyl-morpholin-4-yl)-1-propanol) of the formula

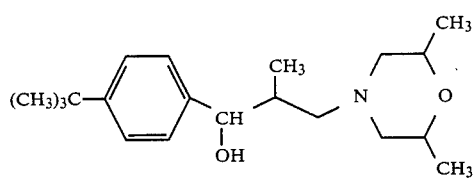

or a physiclogically acceptable acid addition salt thereof.

3. A compound according to claim 1, wherein such compound is 1-(p-tert.-butyl-phenyl)-2-methyl-3-(morpholin-4-yl)-1-propanol of the formula

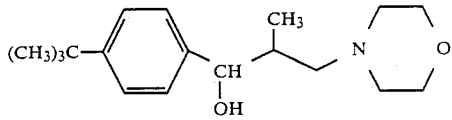

or a physiologically acceptable acid addition salt thereof.

4. A fungicidal composition comprising a fungicidally effective amount of a compound or salt according to claim 1 in admixture with a diluent.

5. A method of combating fungi comprising applying to the fungi, or to a habitat thereof, a fungicidally effective amount of a compound or salt according to claim 1.

6. The method according to claim 5, wherein such compound or salt is selected from the group consisting of
- 1-(p-tert.-butyl-phenyl)-2-methyl-3-(2,6-dimethyl-morpholin-4-yl)-1-propanol,
- 1-(p-tert.-butyl-phenyl)-2-methyl-3-(morpholin-4yl)-1-propanol and
- physiologically acceptable acid addition salts thereof.

* * * * *